United States Patent [19]
Papp et al.

[11] Patent Number: 5,422,272
[45] Date of Patent: Jun. 6, 1995

[54] IMPROVEMENTS TO APPARATUS AND METHOD FOR ELECTROPORATION

[75] Inventors: Andrew A. Papp, 12012 Goshen Ave., #103, Los Angeles, Calif. 90049; John V. Biondo, Jr., Los Angeles, Calif.

[73] Assignee: Andrew A. Papp, Los Angeles, Calif.

[21] Appl. No.: 92,243

[22] Filed: Jul. 14, 1993

[51] Int. Cl.⁶ .................. G12N 15/00; G12N 15/09; C12N 13/00
[52] U.S. Cl. .................. 435/287; 435/173.4; 435/173.5; 435/173.6; 435/173.7; 935/85; 935/93
[58] Field of Search ............... 435/173.4, 173.5, 173.6, 435/173.7, 287; 935/52, 85, 87, 89, 93, 94; 310/339

[56] References Cited

U.S. PATENT DOCUMENTS

| | | | |
|---|---|---|---|
| 3,967,141 | 6/1976 | Gawlick et al. | 310/339 |
| 4,623,814 | 11/1986 | Konda et al. | 310/339 |
| 4,750,100 | 6/1988 | Ragsdale | 363/83 |
| 4,800,163 | 1/1989 | Hibi et al. | 435/287 |
| 4,910,140 | 5/1990 | Dower | 435/172.3 |
| 4,970,154 | 11/1990 | Chang | 935/52 X |

FOREIGN PATENT DOCUMENTS 63-59892 3/1988 Japan .................. 435/173.6

OTHER PUBLICATIONS

E. Neumann, M. Schaefer-Ridder, Y. Wang and P. H. Hofschneider. Gene Transfer into Mouse Lyoma Cells by Electroporation in High Electric Fields. EMBO J.1(7) pp. 841–845 1982.

E. Tekle, R. Dean Astumian, and P. Chock. Electroporation by Using Bipolar Oscillating Electric Field: An Improved Method for DNA Transfection of NIH 3T3 Cells. Proc. Nat'l Acad. Sci. USA vol. 88 pp. 4230–4234 May 1991.

*Primary Examiner*—John Niebling
*Assistant Examiner*—John S. Starsiak, Jr.

[57] ABSTRACT

A new quickly replaceable electrode assembly for electroporation that also provides the functions of a pipette, capable of sucking up samples; applying extremely high electric field strength to samples at lower, safer voltages due to close spacing of the electrode plates; and expelling samples quickly and completely; along with a quick-connect receptacle for the electrode assembly. New methods are detailed for construction of electrode assemblies, providing electric current, monitoring characteristics of electric pulses delivered to samples, and space saving hand held units using low voltage D.C., A.C. line, and piezoelectric power supplies, with peak current delivered indicators are disclosed.

25 Claims, 7 Drawing Sheets

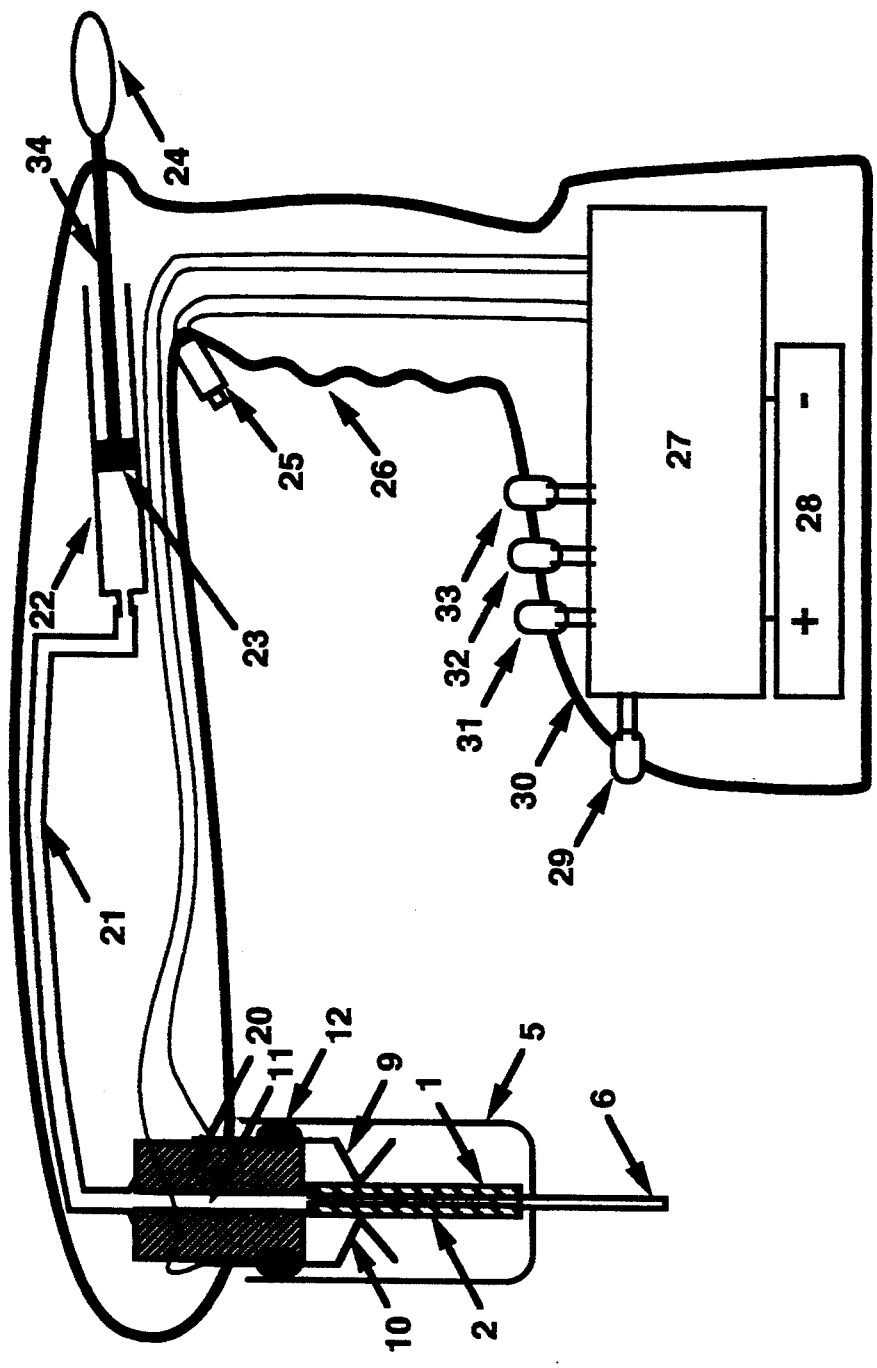

IMPROVEMENTS TO APPARATUS AND METHOD FOR ELECTROPORATION

BACKGROUND OF THE INVENTION

A wide variety of important procedures in biological research and biotechnology involve getting certain materials in to and out from cells. These procedures include gene cloning, DNA library construction, cell fusion, production of cloned proteins, tests on the effects of inserting certain materials into cells, and collection of certain materials found inside cells. Furthermore, these procedures must often be carried out on a large number of independent samples which must not be cross-contaminated. Electroporation, the transient formation of small holes in dielectrics in response to electric fields, provides a means of perforating the cell membrane for accomplishing these procedures (Neumann et al., 1982, EMBO J. 1:841–845).

Prior art electroporation equipment is comprised of large high voltage power supplies capable of producing substantial current at up to 2500 volts, such as that disclosed by Ragsdale on Jun. 7, 1988 in U.S. Pat. No. 4,750,100. Power supplies generating various waveforms, including rectangular, unipolar, bipolar, exponential decay, and radio frequency, are attached via a switching and/or timing means to a sample chamber in which electrodes are spaced to give a field strength appropriate to form pores in the cells of interest (Tekle et al., 1991, PNAS. 88:4230–4234). Existing devices such as that disclosed in U.S. Pat. No. 4,800,163 by Hibi et al. in 1989, are large, expensive, complex, and are more efficient for bulk industrial processing than for the processing of the dozens of individual samples more common in research laboratory work. In working with such samples, which must not be cross-contaminated, it is necessary to replace the electrode assembly with a clean, sterile electrode assembly before each sample is processed. It is an object of the present invention to provide an economical, easily and quickly replaceable, electrode assembly and associated apparatus especially well suited for research laboratory use. Because of the potentially lethal voltage/current combination, sample chambers are usually hidden in protective enclosures with safety interlocks to keep the user at a distance from the high voltage. While such an apparatus provides a reliable means of delivering voltage to a sample, it occupies considerable space and requires complex and time-consuming manipulations to insert and remove samples. Aside from the tedium and high labor cost, there is another significant problem with the prior art apparatus. As described by Dower in U.S. Pat. No. 4,910,140, Electroporation of Prokaryotic Cells, on Mar. 20, 1990, the efficiency of recovering live cells containing molecules of interest falls rapidly as time increases.

The improvements to electroporation of the present invention eliminate the tedium of a human operator as well as increase the survival of electroporated samples due to reduced time under hostile conditions. Some prior art instruments provide numerical feedback relating to current, voltage and wave shape parameters of the delivered energy. The present invention simplifies operation by providing go/no go indicator lights instead of confusing numerical information.

Because only brief pulses of high current are required, a number of options other than the typical bulky continuous duty high voltage power supply are disclosed. In the preferred embodiment of the present invention, a small Direct Current inverter type transformer is used in "flyback" mode to store charge in a capacitor for subsequent discharge. In electrotransfection experiments with E. coli bacteria, efficient transformation was observed using Alternating Current sources including 120 volt 60 hertz line power. Therefore an alternate embodiment of the present invention eliminates the high voltage supply altogether and substitutes the timed application of A.C. line current directly to the sample. The rapid mechanical deformation of piezoelectric crystals provides a high voltage pulse. Therefore in a third embodiment of the present invention the high voltage power supply is comprised of a piezo-electric crystal and mechanical trigger. Because of the electrode assembly's pipetting feature in the present invention, electrodes can advantageously be spaced more closely than in prior electroporation equipment, thus lower voltages can be employed to achieve the desired field strength. This invention provides a system more compact and safe, yet much less complicated and expensive than other systems, for example U.S. Pat. No. 4,750,100 mentioned above.

SUMMARY OF THE INVENTION

One object of this invention is to provide a faster, safer, more economical and efficient method and apparatus for transiently forming holes in dielectrics, such as cell membranes, by the application of a controlled electric field (electroporation). This is accomplished through improved designs of the electrode assembly, electrode receptacle, power supply, and user feedback. For the sake of clarity, throughout this disclosure, "electrode" is defined as any single element that is conductive to electron flow, and "electrode assembly" is defined as any device comprised of an electrode and at least one other element such as another electrode and/or a housing that contains at least one electrode. In the present invention, electrode assemblies with an airtight interelectrode cavity and quick-connect pressure and electrical interfaces are constructed such that samples can be drawn between the electrodes by reducing the pressure in the cavity and expelled by increasing the pressure in the cavity. Positive and negative pressure can be generated in a variety of ways, such as via: a syringe-type piston and cylinder; a peristaltic pump; and deformation of the electrodes, spacer, or separate connected air bladder. The electrode assemblies are used in conjunction with an apparatus comprising a compact power supply, simple user feedback, and an electrode assembly receptacle with a combined electrical and pressure quick-connect interface complementary to the specific electrode assembly.

The foregoing and various other objects and features of this invention will be apparent and fully understood from the following detailed description of the typical preferred forms and applications thereof, throughout which description, reference is made to the accompanying drawings in which

THE DRAWINGS

Figure 4A:
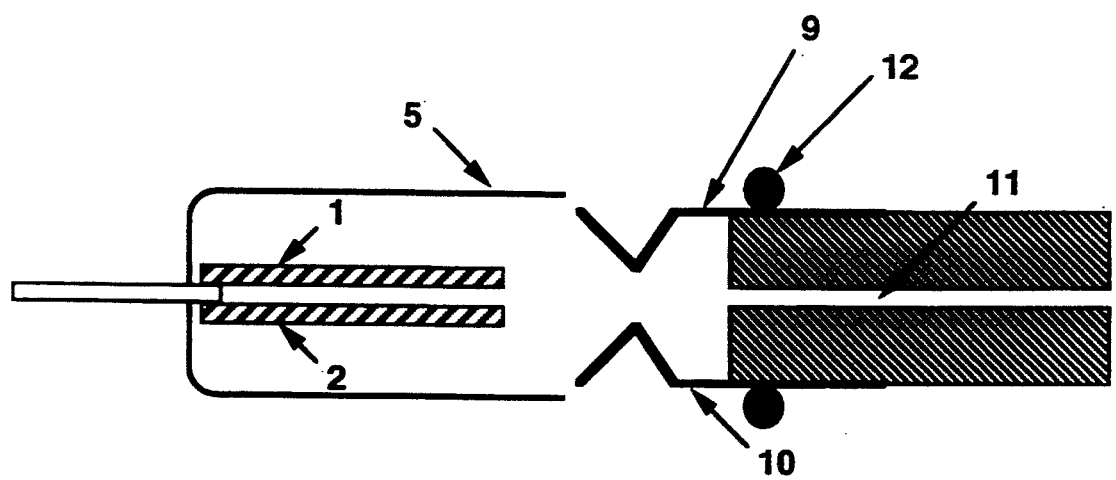
FIG. 4A is a drawing in cross section of an electrode and an electrode receptacle before electrode insertion.
Figure 4B:
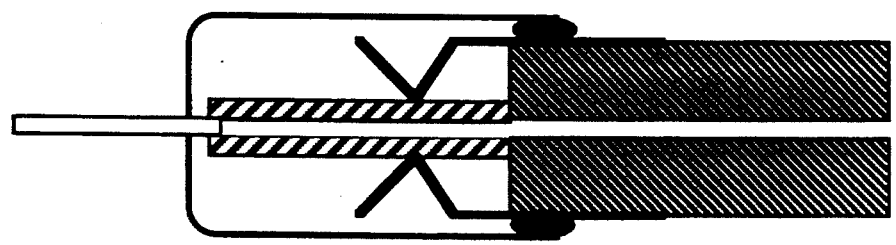
FIG. 4B is a drawing in cross section of an electrode and an electrode receptacle after electrode insertion.
Figure 5:
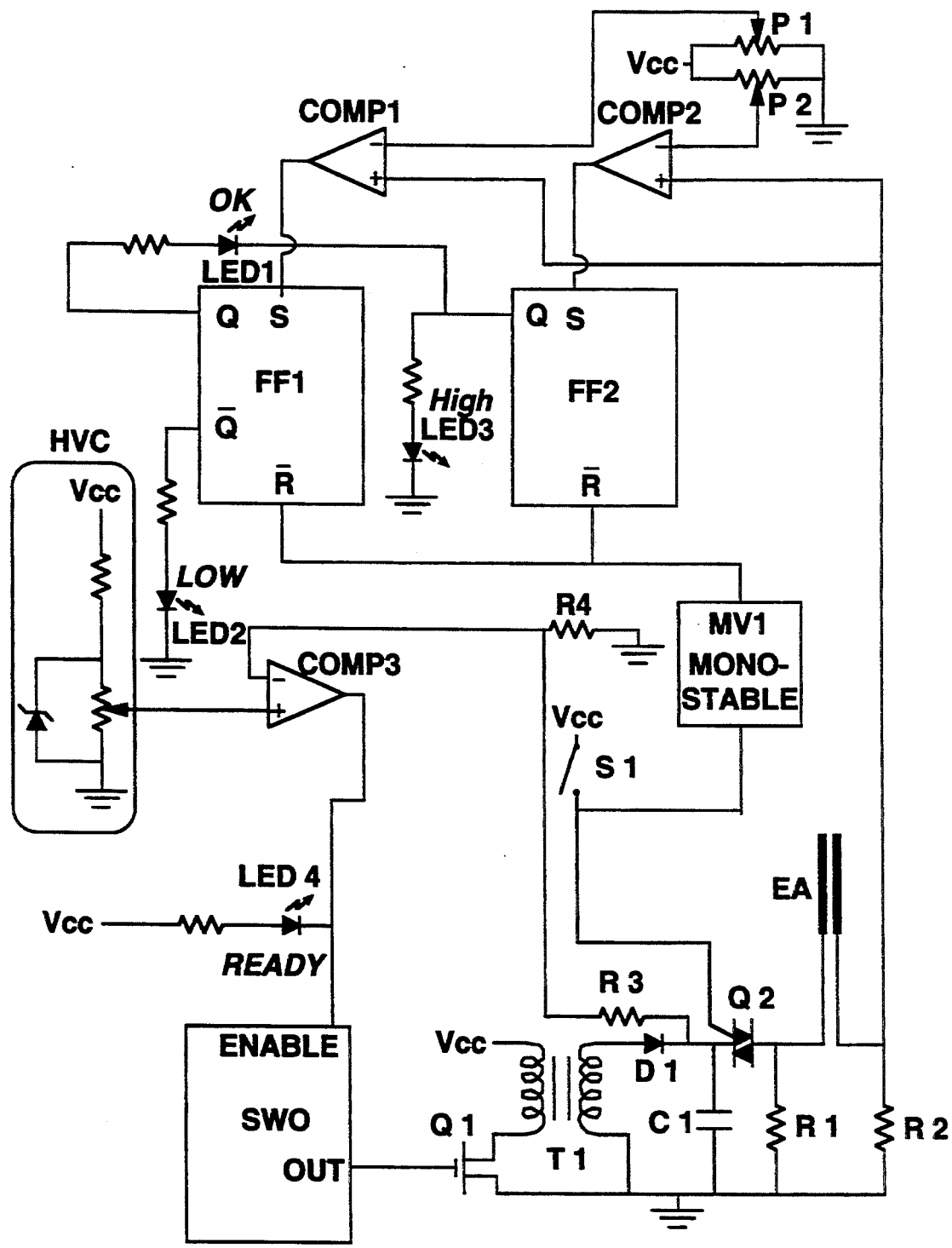
FIG. 5 is a schematic of a high-voltage, Direct Current, electric pulse generator with user feedback indicators.

FIG. 7 is a drawing of a handheld embodiment of the present invention, comprised of the electrode assembly and electrode receptacle of FIG. 4B, the high-voltage, Direct Current electric pulse generator and user feedback indicators of FIG. 5, a thumb operated means to control air pressure within the electrode assembly, rechargeable batteries, and associated wiring and plumbing, all housed in an ergonomic pistol shaped enclosure.

PREFERRED EMBODIMENT

Improvements to electroporation are provided in which electrode assemblies are manufactured with extremely small interelectrode gaps of less than 1 mm, and preferably less than 0.5 mm. Moreover, the electrodes are arranged such that samples can be drawn between or expelled directly from the electrode assembly by applying a negative or positive pressure, respectively. Alternately, the electrode assembly can be maintained at ambient pressure and the sample can be inserted or removed by positive or negative application of pressure to the sample, respectively.

Figure 1:
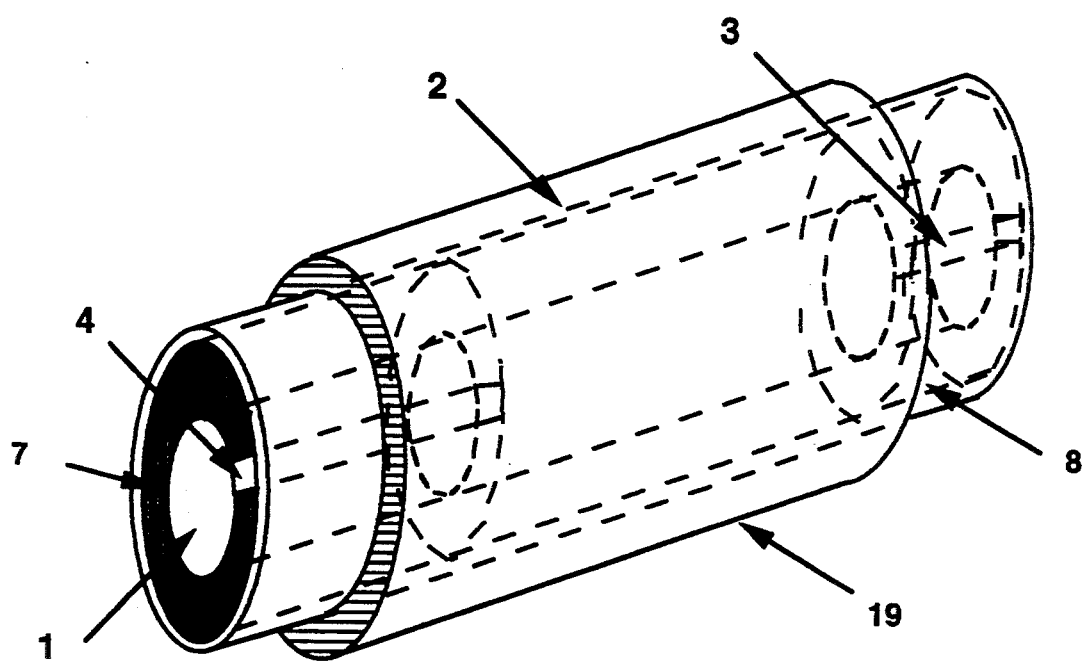
FIG. 1 is a drawing of a coaxial suction electrode assembly with an optional temperature regulating element.
Figure 2A:
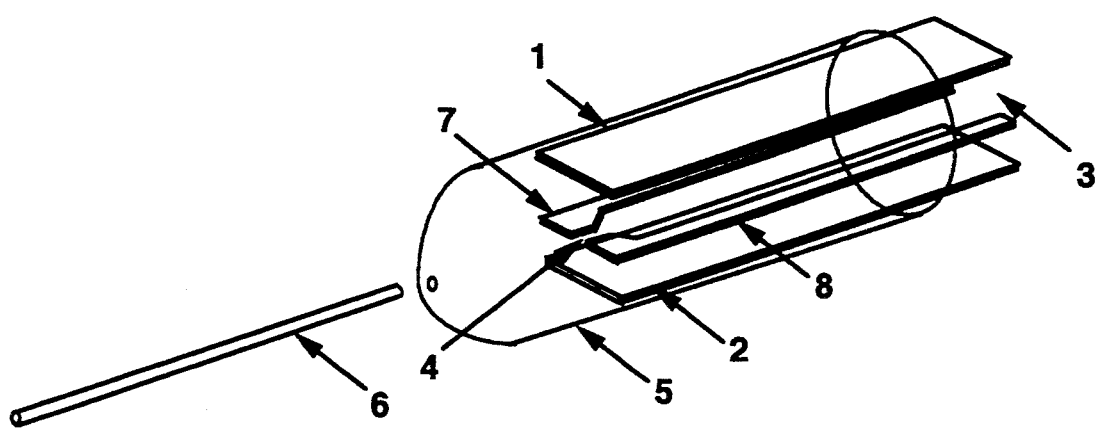
FIG. 2A is a drawing of a parallel suction electrode assembly in exploded view.
Figure 2B:
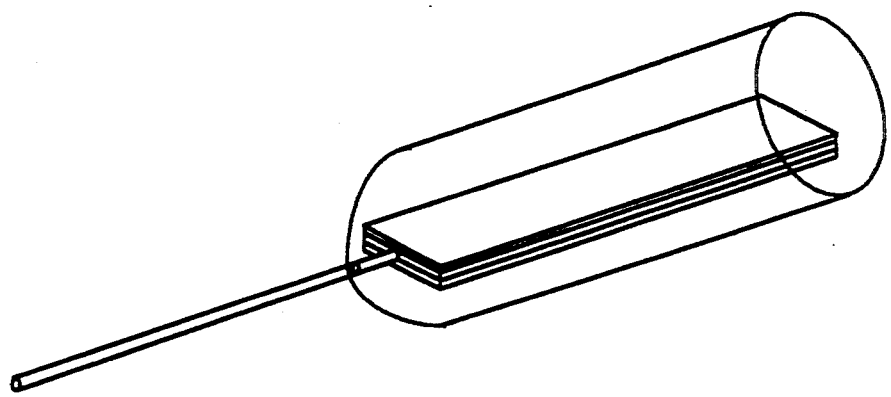
FIG. 2B is a drawing of an assembled parallel suction electrode assembly.

An invention having these purposes is described below with examples of preferred embodiments. FIGS. 1 and 2 each show possible embodiments of a two-electrode quick-connect pipetting electrode assembly. In FIG. 1, the electrodes 1 and 2 are arranged coaxially; whereas in FIG. 2, the electrodes 1 and 2 are arranged as flat parallel plates. In FIGS. 1 and 2, spacer elements 7 and 8 serve to separate the electrodes electrically and mechanically, as well as to provide a leak proof seal. For certain uses, such as in biological applications, it is important for cell viability to hold the cells at a particular temperature during experimental manipulations. To regulate the temperature of cells during electroporation the electrode assembly can be sheathed by a substance with a high specific heat. In FIG. 1, electrode 2 is surrounded by, and in thermal contact with, optional temperature regulation element 19. The temperature regulation element can be fitted to either the electrode assembly or receptacle. For manufacturing purposes, the spacer can be molded in place out of a hardenable adhesive dielectric substance between the electrodes, thereby holding the assembly together in addition to maintaining interelectrode spacing. To draw a sample in between electrodes 1 and 2, a negative pressure is applied to spacer pressure control hole 3, optionally via adapter tube 5. As pressure in the gap between electrodes 1 and 2 decreases below the ambient pressure outside of electrodes 1 and 2, the resulting suction draws sample material, optionally via adapter tube 6, through sample passage way 4 into the gap between electrodes 1 and 2 to equalize the pressure. At this point, the sample can be electroporated by an electric field applied via electrodes 1 and 2. Finally, the sample is expelled from the electrode assembly when a positive pressure is applied to spacer pressure control hole 3, optionally via adapter tube 5, causing the sample to blow out through sample passageway 4, and optionally through adapter tube 6.

Alternatives to each of the embodiments described above are evident if either the electrode(s) or spacer element(s) are flexible and elastic or flexible and inelastic. In these alternative embodiments, pressure control hole 3 is absent, thus the end of the pipetting electrode assembly opposite sample entry hole 4 is sealed. In the flexible embodiments, samples are drawn in by physically compressing the electrode assembly, expelling air in the gap between electrodes 1 and 2, then reducing the compression, in the case of flexible elastic embodiments, or spreading the electrodes mechanically, in the case of flexible inelastic embodiments. As the volume of the gap increases, pressure in the gap falls, causing a sample in contact with entry hole 4, or optionally adapter tube 6, to be drawn in between electrodes 1 and 2. After electroporation, the electrode assembly is recompressed and the resulting increase in pressure between the electrodes causes the sample to be expelled through sample entry hole 4 and optionally through adapter tip 6.

Figure 3A:
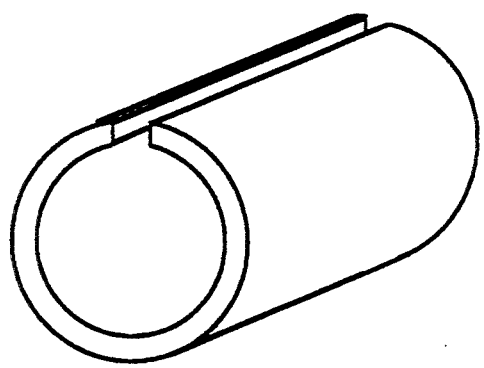
FIG. 3A is a drawing of a heat activatable memory plastic spacer before heat-activation.
Figure 3B:
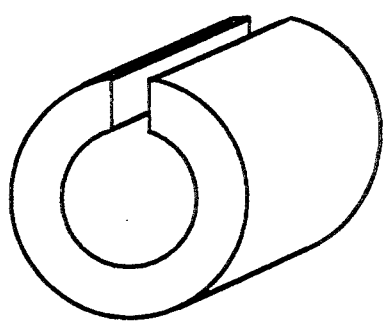
FIG. 3B is a drawing of a heat activatable memory plastic spacer after heat-activation.

A preferred new method for concentrically positioning coaxial elements, such as in the coaxial quick-connect pipetting electrode assembly of FIG. 1, is through the use of an activatable memory plastic (e.g. "heat-shrinkable plastic"). These plastics have a particular spatial conformation which they "remember". Such plastics can be deformed and "frozen" in the deformed state. However, upon "activation", they return toward the conformation they "remember". FIG. 3A shows a spacer appropriate for the coaxial electrode assembly of FIG. 1, fashioned of a heat-activatable memory plastic in the deformed and frozen state. FIG. 3B shows the result, after heat-activation: The plastic returns to its original thicker and shorter "memory conformation". If placed loosely in the gap between the rod and tube electrodes (FIG. 1, electrodes 1 and 2, respectively), the memory plastic will center the rod within the tube as the spacer thickens evenly.

FIGS. 4A and 4B show one preferred embodiment of a quick-connect/quick-disconnect receptacle for suction electrode assemblies such as in FIG. 2. As the electrode assembly is inserted into the receptacle, electrodes 1 and 2 establish electrical contact with receptacle contacts 9 and 10. Simultaneously, electrode assembly adapter tube 5 establishes an air-tight connection with receptacle pressure interface 11, insured by compliant seal 12. Thus, with a single insertion step, both electrical and pressure contacts are formed between electrode assembly and receptacle, and held by friction.

FIG. 5 shows an example of a preferred embodiment of circuitry for the high-voltage generation, pulse discharge, and current-monitoring portions of an electroporation apparatus powered by a low-voltage, Direct Current (D.C.) source such as an electrochemical cell or a line operated, low-voltage D.C. power supply. In this D.C. to D.C. step up high voltage power supply, Square Wave Oscillator SWO provides pulses to switching transistor Q1, typically at 3000 to 5000 Hz.

During each pulse by SWO, Q1 is switched to conduct Vcc to the primary of step-up transformer T1, producing a magnetic field in T1. At the end of the SWO pulse, Q1 is switched off, allowing the magnetic field in T1 to collapse rapidly, thereby producing a high voltage in the output secondary of T1. The output of T1 is converted to D.C. via rectifier D1 and charges capacitor C1. The voltage on C1 is applied to comparator COMP3 via voltage divider R3 and R4. COMP3 compares this voltage with a user-adjustable voltage from High Voltage Control HVC. The user-adjustable voltage is typically set based on empirical studies of electroporation efficiency. When the voltage from C1 rises to the level at which comparator COMP3 changes state, SWO is disabled. As the voltage on C1 fluctuates about the level at which comparator COMP3 changes state, SWO is enabled and disabled appropriately, thereby regulating the voltage on C1.

The change in COMP3 state also causes "ready" light LED4 to conduct and light, informing the user that the apparatus is charged for use. Closing S1, discharges capacitor C1 into R1, R2, and the Electrode Assembly EA, via triac Q2; and clears flip-flops FF1 and FF2 via monostable MV1 with a typical pulse width of 1 microsecond. COMP1 and COMP2 compare the voltage drop caused by the discharge of C1 across R2 with the voltages set by user adjustable P1 and P2, respectively. When the voltage across R2 exceeds neither the P1 or P2 voltage, flip-flops FF1 and FF2 are not set, causing Low-Current Indicator LED2 to light. When the voltage across R2 exceeds the P1 voltage, but not the P2 voltage, FF1, but not FF2, is set, causing OK-Current Indicator LED1 to light. When the voltage across R2 exceeds both the P1 and P2 voltages, flip-flops FF1 and FF2 are set, causing High-Current Indicator LED3 to light. Thus, the indicators LED1, LED2, and LED3 inform the user of the peak current range of the current discharge through the electrode assembly.

Figure 6A:
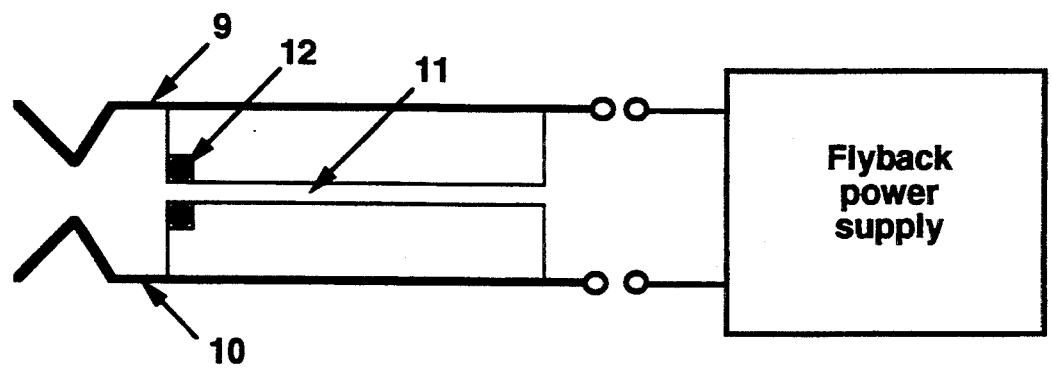
FIG. 6A is a drawing showing the electrical connection of the flyback power supply of FIG. 5 to the electrode receptacle of FIG. 4A.
Figure 6B:
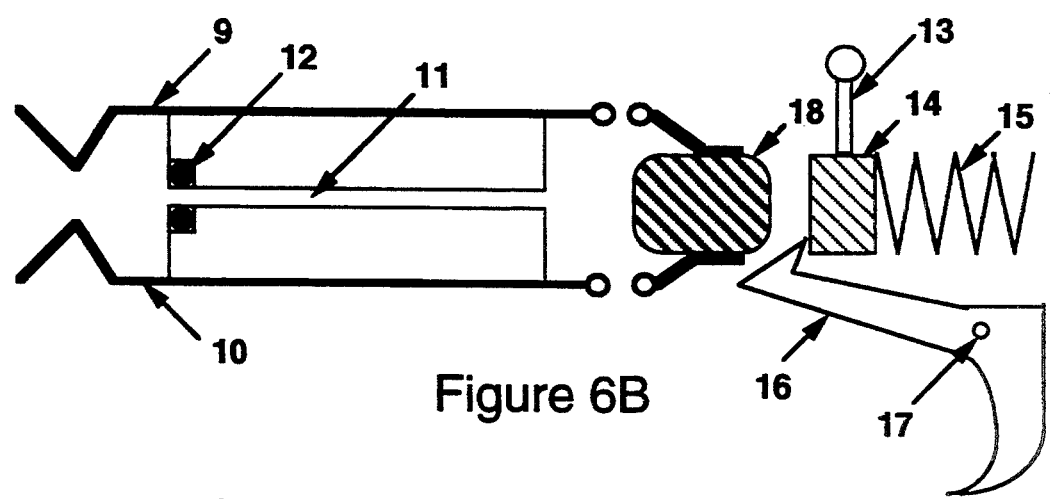
FIG. 6B is a drawing demonstrating how a piezoelectric crystal can be used to apply a voltage pulse to the electrode receptacle of FIG. 4A.
Figure 6C:
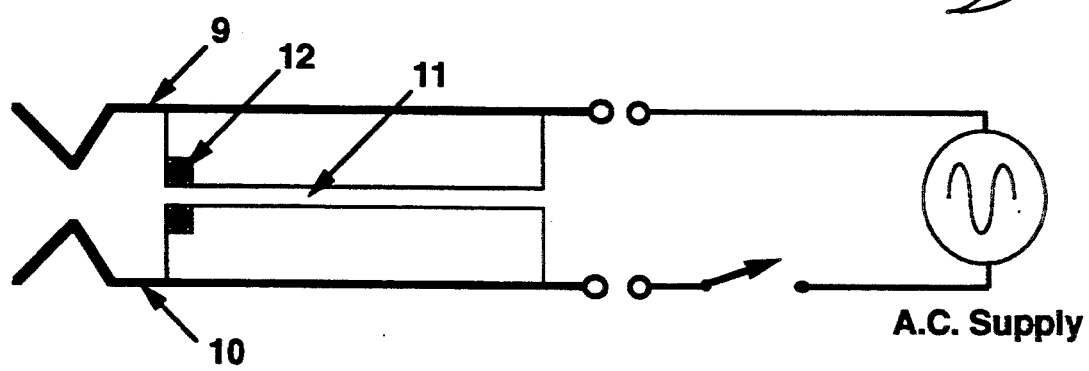
FIG. 6C is a drawing demonstrating how an Alternating Current supply can be used to apply a voltage pulse to the electrode receptacle of FIG. 4A.

In this embodiment, a small flyback transformer is utilized to produce a D.C. to D.C. step up high voltage power supply and charge a capacitor until sufficient energy is stored, since energy need only be delivered periodically; thus, a bulky continuous current, high-voltage power supply is not required. In alternate embodiments, the entire D.C. power supply of the previous embodiment can be omitted, and instead, either a timed Alternating Current line source as in FIG. 6C, or a piezo-electric power source as in FIG. 6B, can be substituted for acceptable results at a tremendous savings in equipment, cost, size, and weight. In FIG. 6B hammer 14 can be retracted against spring 15 via handle 13. Latch 16, pivotably mounted on pin 17, holds hammer 14 against the force of spring 15 until hammer 14 is released by finger pressure against the curved section of latch 16. Spring 15 will then force hammer 14 forcibly against piezo-electric element 18 causing an electrical pulse to be generated by the piezo-electric element 18. The voltage pulse generated by piezo-electric element 18 is conducted to the electrode assembly via contact 9 and contact 10.

FIG. 7 shows an especially easy to use, handheld, battery operated embodiment of the disclosed invention incorporating an electrode receptacle with its complementary disposable parallel plate electrode assembly. Except for the disposable electrode assembly, the entire unit is encased in ergonomic gun body 30. The user picks up the unit at ergonomic hand grip 26. Prior to use, the electrode assembly is attached to the electrode receptacle. In a single inserting motion, electrodes 1 and 2 establish connection with electrode receptacle contacts 9 and 10 while adapter tube 5 establishes an airtight seal with electrode receptacle body 20 via compliant seal 12. Rechargeable battery 28 powers circuit board 27. When an appropriate charge for electroporation is stored in circuit board 27, ready light 29 becomes illuminated. The user inserts thumb into thumb ring 24, and inserts electrode adapter tube 6 into a sample to be electroporated. With a backward thumb motion in thumb ring 24, the user partially withdraws piston 23 from cylinder 22 via connecting rod 34. This operation creates a negative pressure in cylinder 22 which is applied to the cavity between electrodes 1 and 2 via tube 21 and pressure receptacle interface 11, causing the sample to be drawn between electrode plates 1 and 2 via adapter tube 6. The user then activates trigger switch 25 causing circuit board 27 to discharge an appropriate electrical waveform (such as an 800 volt, 5 millisecond exponential decay) across the sample between electrodes 1 and 2 (interelectrode distance of 0.5 millimeters) to effect electroporation. Indicator lights 31, 32, and 33 inform the user whether the peak current discharged through the sample was normal, or too low, or too high for effective electroporation. After electroporation, the sample is ejected when the user moves thumb ring 24 forward, compressing air in cylinder 22 with piston 23 via connecting rod 34. The pressure is applied to the cavity between electrodes 1 and 2 via tube 21 and pressure receptacle interface 11 causing the sample to be expelled through adapter tube 6.

From the foregoing it will be understood that the preferred embodiments have features which enhance performance under certain conditions while limiting performance under others; however, the scope of this invention is not limited by said features. The foregoing and various other objects and features of this invention will be apparent and fully understood from the detailed description of the typical preferred forms and applications thereof, throughout which description, reference is made to the accompanying drawings.

What we claim is:

1. An apparatus for electroporation or the like comprising:
    a) receptacle means for providing an interface to a voltage having a predetermined waveform and a source of positive and negative pressure,
    b) an electrode assembly including at least two electrodes gapped by at least one spacer, said electrode spacer combination forming a cavity,
    c) one port to said cavity,
    d) means for removably coupling said electrode assembly to said receptacle means, wherein said electrode assembly is coupled to said receptacle means, positive and negative pressure is selectably applied to said cavity, and said voltage is applied to said electrodes during a predetermined period of time.

2. The apparatus as set forth in claim 1, wherein spacing between said two electrodes is less than 1 millimeter.

3. The apparatus as set forth in claim 1, wherein spacing between said two electrodes is less than 0.5 millimeter.

4. The apparatus as set forth in claim 1, further comprising means for regulating the temperature of said electrode assembly.

5. The apparatus as set forth in claim 1, wherein at least one of said electrodes and said spacer are flexible.

6. The apparatus as set forth in claim 1, wherein said spacer is composed of a hardenable adhesive.

7. The apparatus as set forth in claim 1, wherein said cavity between said two electrodes is maintained by heat activated memory plastic.

8. The apparatus as set forth in claim 1, wherein said port connects to an elongated adapter tube, said adapter tube having an inside diameter of less than 6 millimeters and a length of greater than 2 millimeters.

9. The apparatus as set forth in claim 1, with at least one additional port through which to control said pressure within said cavity.

10. The apparatus as set forth in claim 1, wherein the surfaces of said electrodes are flat.

11. The apparatus as set forth in claim 10, wherein at least one of said electrodes and said spacer are flexible.

12. The apparatus as set forth in claim 10, wherein said spacer is composed of a hardenable adhesive.

13. The apparatus as set forth in claim 1, wherein said electrodes are coaxial.

14. The apparatus as set forth in claim 13, wherein said port connects to an elongated adapter tube, said adapter tube having an inside diameter of less than 6 millimeters and a length of greater than 2 millimeters.

15. The apparatus as set forth in claim 13, wherein the spacer consists of heat activated memory plastic.

16. The apparatus as set forth in claim 1, wherein said voltage is generated by a Direct Current inverter high voltage power supply.

17. The apparatus as set forth in claim 1, wherein said voltage is Alternating Current line voltage applied via a switch to said electrode assembly to effect electroporation or the like.

18. The apparatus as set forth in claim 1, wherein said voltage is generated by a piezoelectric voltage source to effect electroporation or the like.

19. The apparatus as set forth in claim 1, further comprising a means for indicating peak current flow between said electrodes.

20. An electrode assembly receptacle for an electroporation apparatus comprised of a voltage source and an electrode assembly comprising:
   means for concurrently establishing removable pressure connection with said electrode assembly and removable electrical connections with said electrode assembly.

21. The electrode assembly receptacle as set forth in claim 20, wherein at least one of said pressure connection and said electrical connections are compliant.

22. An electrode assembly for an electroporation apparatus comprised of a voltage source and an electrode assembly comprising:
   a) at least two electrodes gapped by at least one spacer, said electrode spacer combination forming a cavity,
   b) at least two ports into said cavity,
   c) a unified connection means for removable attachment to both an electrical source and at least on of said at least two ports for controlling pressure within said cavity.

23. An apparatus for electroporation or the like comprising:
   a) a chamber including at least two electrodes,
   b) a DC to DC step up high voltage power supply,
   c) a capacitor for storage of said high voltage,
   d) a switching means for directing said high voltage to said electrodes.

24. An apparatus for electroporation or the like comprising:
   a) a chamber including at least two electrodes, said electrodes spaced at most 1 millimeter apart,
   b) an Alternating Current line voltage source the voltage being less than 300 volts and the frequency being less than 10 kilohertz,
   c) a switching means for directing said line voltage to said electrodes.

25. An apparatus for electroporation or the like comprising:
   a) a chamber including at least two electrodes
   b) a piezo-electric voltage source,
   c) means for directing said voltage to said electrodes.

* * * * *